United States Patent [19]  [11]  4,151,130
Adams  [45]  Apr. 24, 1979

[54] POLYMER MODIFIED CELLULOSE FIBERS AND METHOD OF PRODUCING

[75] Inventor: James W. Adams, Schofield, Wis.

[73] Assignee: American Can Company, Greenwich, Conn.

[21] Appl. No.: 874,667

[22] Filed: Feb. 2, 1978

[51] Int. Cl.² ............................................. C08L 1/08
[52] U.S. Cl. ........................................... 260/17.4 GC
[58] Field of Search .............................. 260/17.4 GC

[56] References Cited

U.S. PATENT DOCUMENTS

| | | | |
|---|---|---|---|
| 3,194,727 | 7/1965 | Adams et al. | 1622/168 |
| 3,256,372 | 6/1966 | Adams et al. | 264/28 |
| 3,366,582 | 1/1968 | Adams et al. | 260/2.5 |
| 3,682,856 | 8/1972 | Adams et al. | 260/17.4 GC |
| 3,721,627 | 3/1973 | Adams et al. | 252/89 |
| 3,793,299 | 2/1974 | Zimmerer | 260/2.2 R |
| 3,838,077 | 9/1974 | Hoftiezer et al. | 260/17.4 GC |
| 4,025,472 | 5/1977 | Lepoutre | 260/17.4 GC |

OTHER PUBLICATIONS

Lepoutre et al., Pulp & Paper Reports PPR145, Pulp & Paper Research Institute of Canada, pp. 1-21, Mar., 1976.

Adams et al., Applied Polymer Symposium, No. 28, pp. 831-843, 1976.

*Primary Examiner*—Maurice J. Welsh
*Attorney, Agent, or Firm*—Robert P. Auber; Ira S. Dorman; George P. Ziehmer

[57] ABSTRACT

This invention relates to improved methods for treatment of polymer modified cellulose fibers to greatly enhance their ability to absorb and retain aqueous fluids, thereby increasing their usefulness in disposable diapers, catamenial and surgical pads and other absorptive, single use pads where utility depends primarily on rapid, high volume fluid absorption and retention. More particularly, this invention relates to the treatment of absorptive fibrous products comprising crumb-hydrolyzed polyacrylate-modified natural cellulose fibers by procedures which permanently swell and condition the fibers so that they are capable of absorbing and retaining much greater volumes of aqueous fluids than the same materials prior to the treatment by the processes of this invention.

13 Claims, No Drawings

POLYMER MODIFIED CELLULOSE FIBERS AND METHOD OF PRODUCING

BACKGROUND OF THE INVENTION

Natural cellulose fibers, such as those obtained by the pulping of wood by known paper pulp making processes, may be substantially modified in their physical and chemical properties by graft polymerizing selected olefinic monomers in and on the fibers by known reactions carried out in situ in aqueous suspensions of the cellulose fibers. For example, natural cellulose fibers modified by the presence of alkali metal salts of polyacrylic acid chemically united with the cellulose, may be obtained by an in situ polymerization of acrylonitrile in and on papermaking cellulose pulp fibers, followed by a hydrolysis in strong alkali of the nitrile groups present in the polyacrylonitrile portions of the polymer-modified fibers. The preparation of such polyacrylate-modified cellulose fibers has been described in prior art patents, including U.S. Pat. Nos. 3,194,727, 3,256,372, 3,366,582 and 3,682,856, issued to J. W. Adams and H. W. Hoftiezer, 3,793,299 to Zimmer, and, more recently, 3,838,077, issued to H. W. Hoftiezer and A. H. Tilloson, which latter patent describes an improved method for hydrolysis of the polyacrylonitrile-modified fibrous cellulose material at high solids concentration to achieve a material having superior physical properties for use as a viscosity builder and absorptive agent for aqueous media.

To be useful as a principal absorbent medium to be incorporated in disposable diapers and other single use absorptive pads, the absorptive medium must have the capacity to absorb large amounts of fluids rapidly and to retain the absorbed fluids completely, even though the absorptive pad is subjected to twisting, flexing or pressure forces while being worn or held in contact with an active human body. At the same time, the absorbent medium must retain its structural integrity and not shift position substantially in relation to the other pad components, even though the pad is subjected to normal stresses and pressures while substantially saturated with body fluids or exudates.

Certain polymer-modified natural cellulose fibers are well suited to use as an absorptive medium in diapers and other disposable pads. Of particular value are insoluble, fibrous products prepared by treating an aqueous suspension of natural cellulose fibers, such as those obtained by standard pulping procedures from wood, straw or other lignocellulosic plant material, or cellulose fibers from cotton linters, etc., with an ethylenically unsaturated compound containing at least one functional moiety selected from the group consisting of acrylamide, acyl halide, nitrite, ester, alkenyl halide, carboxylate salt and carboxylic acid in the presence of a polymerization catalyst and subsequently hydrolyzing or neutralizing the resultant polymer-modified cellulose fibers under controlled alkaline conditions to obtain alkali metal polymer-modified cellulose fibers. In the preparation of the polyacrylonitrile-modified cellulose product, for example, the reactant ratios are adjusted to yield a product having a polymer-to-fiber ratio of between about 0.5 to 1 and about 5 to 1. If such a product is then subjected to an alkaline hydrolysis with an alkali metal hydroxide, the hydrolysis conditions and subsequent treatment of the reaction product will profoundly influence the properties relating to its utility as an absorptive medium in disposable pads as described hereinbelow.

For example, if the hydrolysis is carried out at low total solids concentration (up to about 25% total solids, for example), the resultant product, although having a high absorption and retention for aqueous fluids, will lack structural integrity when wet, the individual damp fibers easily moving in relation to each other so that the absorbent material readily shifts position in the pad under stress of any kind. The product is thus unsatisfactory for general use as an absorbent medium in a diaper, for example, since the absorbent material, when moist, will be displaced by an infant's weight and movements from the particular areas where absorptive potential is critically needed. If, on the other hand, the hydrolysis is carried out under particularly drastic conditions of temperature and of reagent concentration, the resultant product, while displaying excellent structural integrity so that it retains its position in a composite diaper construction under all normal circumstances of stress or pressure, is nevertheless of less than optimum suitability because of its relatively low fluid absorptive and retentive capacity. Polyacrylate-modified cellulose fibers prepared in accordance with the alkaline pressure hydrolysis described in U.S. Pat. No. 3,793,299 issued to R. E. Zimmerer for synthesis of a non-swelling cellulose-acrylate copolymer of high ion exchange capacity fall in this category.

Even more recently, Lepoutre in U.S. Pat. No. 4,025,472 and in a paper, "The Production of a Fibrous Superabsorbent: Technical and Economic Aspects," *PPRIC of Canada,* March, 1976, has proposed methods to provide wood pulp modified by graft-polymerization of polyacrylonitrile which is subsequently hydrolyzed to give improved water absorption properties.

In general, thickeners, adhesives or super absorbents may be produced by hydrolyzing graft copolymers of acrylonitrile and cellulose in wood pulp resulting in at least three different products in terms of chemical and physical properties which may be loosely characterized as (1) difficult-to-dry, discreet fibers types derived from paste hydrolysis; (2) easy-to-dry, hard gel fiber clusters types derived from crumb hydrolysis and (3) hard fiber aggregates types derived from high pressure hydrolysis.

To understand the differences between the various products and procedures, a consideration of the course of the hydrolysis is helpful. For example, alkaline hydrolysis of the nitrile groups on polyacrylonitrile to sodium carboxylate groups proceeds through an amide intermediate:

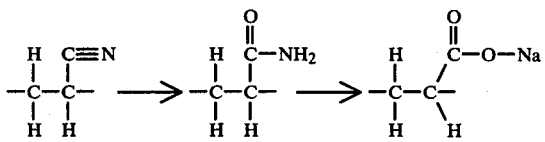

Because of neighboring group effects, hydrolysis is never complete and a combination of carboxyl and amide groups is obtained. The ratio of carboxyl to amide groups in hydrolyzed polyacrylonitrile modified-cellulose products therefore depends on reacting conditions.

In the case of paste hydrolysis where alkali concentrations range from about 1.0 to 15% in water, the polyacrylamide content of cellulose grafts ranges from about 40 to 60%. The products are discrete fibers and although paste hydrolysis procedures are capable of yielding highly absorbent product as indicated by LePoutre, the actual product yield in general has been very low, as much as 50% or more of product in general being lost in washing. Additionally, after washing, the paste of swollen fiber fragments is very difficult to dry so that solvent treatment to agglomerate fibers and remove water is required.

Easy-to-dry, hard gel fiber clusters from crumb hydrolysis after aging in accordance with U.S. Pat. No. 3,838,077, and after grinding, are suitable water-base thickeners but exhibit only poor-to-fair qualities as superabsorbents while hard-gel aggregates as in U.S. Pat. No. 3,793,299 are suitable primarily as ion-exchange resins.

SUMMARY OF THE INVENTION

The present invention is directed to highly absorbent fibers derived from the second product type discussed above, i.e. easy-to-dry hard gel fiber clusters from crumb-hydrolysis and method of producing the same. The products of the invention may be generally characterized as firm-to-loose gel clusters derived by using certain aging and washing procedures to further modify crumb-hydrolyzed polymer-modified cellulose. The invention is discussed with particular reference to polyacrylonitrile modified cellulose which is hydrolyzed to polyacrylate-modified cellulose material. However, it will be understood that the method is equally applicable to such fibers modified with ethylenically unsaturated compound containing functional moieties capable of being hydrolyzed or neutralized such as acrylamide, acyl halide, nitrile, ester, alkenyl halide, carboxylate salt and carboxylic acid as described herein above. Typical of such compounds having such functional moieties are: acrylamide, acrylonitrile, methacrylonitrile, acrylic esters, methacrylic esters, vinyl acetate, acrylyl chloride, vinylidene cyanide, maleic anhydride, maleimide, fumaramide, acrylic acid, methacrylic acid, maleic acid, fumaric acid or their alkali metal salts and combinations of such compounds.

It has now been found that the fluid absorptive and retentive properties of alkali metal polymer-modified cellulose fibers prepared by previously known methods and particulary by the procedure which involves an alkaline hydrolysis of PAN-modified fibers at high solids concentration (30–60% total solids) may be greatly enhanced by certain soaking, washing, swelling and aging procedures carried out subsequent to the hydrolysis under controlled conditions according to the dictates of this invention, as will be detailed hereinafter.

To obtain polyacrylate-modified fibers having, in optimum combination, both a high water retention value (WRV) or saline retention value (SRV) and a high degree of structural integrity under stress, it is necessary according to this invention that the polyacrylonitrile-modified cellulose fibers be hydrolyzed at total solids concentrations in the range of 35-60% preferably between 40 and 55%, and then be subjected to controlled periods of aging and subsequently to steepage or soaking in an aqueous medium, which opens and swells the agglomerated, fibrous structure and thereby contributes both to the WRV and the stress resistance of the final, dried hydrolysis product.

DETAILED DESCRIPTION OF THE INVENTION

It has been found that the water absorption rate (WAR) water retention value (WRV), saline retention value (SRV) and the ability of the particulate agglomerates of polymer-modified cellulosic material fibers to retain their structural integrity under stress as measured by the gel strength are all influenced by (A) the history of the hydrolyzed starting material as it is influenced by (1) the polymer-to-fiber ratio in the polymer-modified cellulose fibers and (2) the conditions under which hydrolysis of the polymer-modified product is carried out; (B) Aging of the hydrolyzed product considering the length of time during which the hydrolysis product is stored after the hydrolysis; (C) Steeping or soaking of the hydrolyzed, aged polymer-modified fiber agglomerates in an aqueous medium for a period of time sufficient to allow the agglomerate structure to swell and expand the internal pore structure thereof, and (D) drying under conditions which maintain the gel strength, once it is so obtained. The structural strength of the agglomerate of fibers which, for simplicity, will be referred to hereinafter as the gel strength, is affected by (1) the temperature at which the swollen gel-like agglomerated particles are dried and (2) by any compressive or grinding forces to which the gel granules are subjected during or after drying. Each of the above factors are interrelated and have an effect on the properties relating to the effectiveness of the polymer-modified fibers in absorptive pads as will be discussed in detail hereinafter.

While not wishing to be limited by any theory of the chemical mechanisms involved in the processes relating to this invention, it is believed that inter-fiber cross-linking of the polymer which is grafted on the cellulose fibers plays a part in the determination of the relative overall absorptive ability of samples of polymer-modified cellulose fibers of varying process history. Samples prepared by a hydrolysis procedure carried out at low solids i.e. up to 25% total solids concentration, exhibit substantially no clumping or agglomeration into a plexus of fibers. It is believed that this may be due to the fact that the distances between fibers during hydrolysis were too great for interfiber polymer bridging to occur. The resultant absorptive product, although high in absorbing capacity, is not a wholly desirable material for use in pads because, when wet, the individual fibers are slippery and slide readily past each other and are easily displaced from their original location in an absorptive pad when subjected to pressure.

When the fibers are packed together during hydrolysis, however, as is the case with hydrolysis reactions carried out at solids concentrations of 35–60%, there is little movement between fibers within the crumb-like particles in the reaction mixture. This presents an excellent possibility for inter-fiber polymeric bonds to form and, in fact, the resulting product, hereinafter referred to as the crumb hydrolysis product, is in the form of granular clumps, agglomerates or clusters of fibers which exhibit a resistance to deformation or disintegration into the individual fibers, even when the product is wet with water. The degree to which the particulate agglomerates of hydrolyzed polymer-modified cellulose fibers resist disintegration when saturated with water increases with an increase in the solids concentration at which the hydrolysis is carried out. It has also been found, however, that the amount of water which will be absorbed and retained by a given weight of polymer-modified fibers decreases with increasing concentration of solids during hydrolysis. It is believed that the degree of structural integrity of the particles or granules of material, or gel strength, as it is referred to in this application, is related to the degree of inter-fiber cross-bridging occurring during the hydrolysis reaction, more cross-bridging being associated with a higher gel strength and also with relatively inferior fluid absorptive properties of the product.

For use in an absorptive pad, both a high fluid absorptive capacity and a high gel strength are desired and materials previously utilized for this purpose have tended to exhibit a deficiency in one or the other of these characteristics. The aging, steeping and swelling process of this invention results in a substantial increase in absorptive characteristics of the polymer-modified cellulose fibers without seriously impairing the gel strength of the particulate product.

Steeping in water at room temperature or at moderately elevated temperatures for periods of time ranging from a few minutes to an hour or more results in a swelling of the particles or granules of agglomerated polymer-modified cellulose fibers, with a substantial resultant increase in volume of each particle. The final, swollen particulate agglomerate is quite porous and therefore absorbs large amounts of fluid rapidly and retains them tenaciously, the water retention value being substantially enhanced in comparison with a sample which has not been steeped in water. The swollen gel is believed to retain to a substantial degree the inter-fiber cross-bridging which presumably took place during hydrolysis and it is this inter-fiber bonding which gives the gel whatever degree of structural integrity it has in a given sample.

The samples of polyacrylate-modified fibers, for example, prepared by hydrolysis at very high solids concentration (60 or 65% solids) have a very strong gel structure and are less responsive to the steeping and swelling process of this invention than samples hydrolyzed at 35–60% solids. It is thought that the inter-fiber bridging is so strong in such samples prepared at the very high solids concentration that the steeping procedure is relatively ineffective in modifying the particulate structure to improve the absorptive properties of the material.

The hydrolysis herein is therefore carried out at between 35% to 60% solids and preferably between about 40 and 55% solids concentration in order that the subsequent steeping and swelling process may bring about the maximum degree of improvement in fluid absorption and retention properties.

It has also been found that changes in the polymer-modified cellulose fibers occur spontaneously on aging the hydrolysis product at room temperature or at moderately elevated temperatures and that some improvement in water absorption and retention capacity generally results from such changes. Products prepared by hydrolysis at very high solids concentration (65% solids) show very little improvement in these properties on aging, whereas products prepared by a 40–55% solids hydrolysis show a very substantial improvement. It is believed that the response of the hydrolysis product to both the aging procedure and to the swelling procedure of this invention is dependent on the material in terms of the number and strength of inter-fiber cross-linking bonds formed during hydrolysis. Products with fewer and/or weaker inter-fiber bonds respond both to aging and to steeping procedures by acquiring improved absorptive properties by a weakening, distending, or in some cases a severing of inter-fiber, cross-bridging bonds. This effect is very desirable, but when the effect is achieved by unduly weakening the gel strength of the particulate masses, the utility of the product in absorptive pads is negated. Products with many and/or very strong inter-fiber bonds have excellent gel strength but are deficient in absorptive properties, which deficiency is not substantially overcome either by aging or by the steeping procedure of this invention, nor by a combination thereof.

The products having the most desirable absorptive and structural properties according to the invention are those which have been (1) prepared by a hydrolysis at about 40–55% solids concentration, (2) allowed to age at room temperature or moderately elevated temperature for a period of at least one, and preferably, from three to six weeks, and (3) subjected to the steeping and swelling procedure of this invention, including steeping in water at room or moderately elevated temperature for a period sufficient to obtain maximum swelling of the granules and then (4) drying under conditions which do not subject the swollen granules to fracturing or grinding pressures or to excessively high temperature. It will be understood that the alkali concentration, e.g. of NaOH, during hydrolysis is constant throughout the description which follows. In general The NaOH or other alkali employed during hydrolysis will range from about 45 and 80 parts of NaOH per 100 parts of polymer-modified fibers, preferably from about 50 to 55 parts NaOH per 100 parts of polymer modified fibers.

A. Crumb Hydrolysis Products

In preparing a polyacrylate-modified cellulose fiber material of satisfactory processing history preliminary to subjecting the product to the aging, soaking and swelling procedures of this invention, standard papermaking cellulose fibers obtained from the pulping of wood by well-known procedures are reacted with acrylonitrile to form a graft polymeric fibrous product in accordance with the teachings of U.S. Pat. No. 3,838,077, previously mentioned. The PAN modified cellulose fibers resulting from the above graft polymerization are then subjected to an alkaline hydrolysis at high solids concentration, also in accordance with the teachings of U.S. Pat. No. 3,838,077 to yield the polyacrylate-modifed fibrous cellulose material which is the starting material of this invention.

The polymerization reaction is carried out in a manner to form, as the product thereof, a PAN-modified cellulosic material having a polymer-to-fiber ratio of between 0.5 to 1 and 5 to 1, the preferred range being between about 1 to 1 and 3.5 to 1.

The source of the cellulose fibers used in the polymer grafting reaction is of relatively slight significance, since fibers from both hardwoods and softwoods are satisfactory, whether prepared by the sulfite, sulfate or soda process for the chemical delignification of the wood fibers. Pulps from Canada as well as all major pulp producing areas of the United States have proven to be of almost equal utility, with southern softwood Kraft pulp being considered the most desirable by a very slight margin over the other pulps tested.

In general terms, the polymerization reaction is carried out as follows: cellulose fibers from a suitable source are suspended in an aqueous medium, a ferrous salt is added and allowed to penetrate the cellulose fiber structure, acrylonitrile is then added together with the hydrogen peroxide portion of the catalyst couple, and the polymerization is carried out under reflux conditions. After carrying out the in situ polymerization for a time sufficient to react the desired amount of monomer with the cellulose fibers to form a polyacrylonitrile-modified cellulosic fibrous material, the remaining monomer is stripped off to leave the grafted cellulose product which is then hydrolyzed in alkali to convert the nitrile groupings to the corresponding alkali metal polyacrylate salts grafted in and on the cellulose fiber framework. The hydrolysis is carried out at high solids (35–60%) content, after which the resulting polyacrylate-modified cellulosic fibers are ready for subsequent treatment in accordance with the procedures of this invention.

The following test procedures used to evaluate the products of the invention are referred to:

Gel Strength

When used in absorbent pads of various types, the absorbent material of this invention is generally used as a filler sandwiched between two cover layers, the inner one of which is porous, while the outer may be either porous or moisture-impermeable. To give satisfactory service, the enclosed absorbent material should retain its structural integrity even when soaked with aqueous fluids so that it does not ooze out of the fiber matrices of the cover sheet or otherwise change its position or structure when the pad is subjected to squeezing or other pressures associated with its attachment to and intimate contact with an active human body. In order to measure the resistance of the absorptive materials of this invention to deformation or displacement under pressure while the materials are saturated with a fluid, a test was devised to determine the force required to extrude the fluid saturated gel-like agglomeration of fibers through a 150 mesh screen. By correlation of the data obtained from this test with the performance of the absorptive products in absorptive pads, it has been determined that a force value of greater than 2 kilograms per square centimeter is desired as being representative of a satisfactory level of structural stability for the absorbent materials to be used in diapers and similar absorptive pads. The test equipment includes a cylindrical cell of 0.625 inch (1.59 cm.) diameter and 1.5 inch (3.8 cm.) height fabricated of Teflon. At the bottom of the cylinder is a 150 mesh stainless steel screen backed, for strength reasons, with a 40 mesh steel screen. The screens are supported on the bottom of the cylinder which is perforated with closely spaced holes of 1 mm. in diameter. The test cell is mounted on a standard Instron tester, which records force as a function of time on a strip chart.

The test procedure is as follows:

One gram of the absorbent material to be tested for gel strength is placed in a 250 ml. beaker with 200 ml. of distilled water. After thorough mixing and standing for one hour, the water-saturated absorbent is transferred to a filter paper on a suction filter and retained for testing. The saturated material is packed under light pressure into the test cylinder which is mounted in the Instron tester adjusted to move the piston into the cylinder at the rate of one inch per minute, thus extruding the absorbent gel through the 150 mesh screen at the bottom of the test cell. The force required to perform the extrusion is continuously recorded and a force value (F) is selected from the flat portion of the stress-strain curve where extrusion conditions are equilibrated. The gel strength in kilograms per square centimeter is calculated as 0.228 F, where F is the force in pounds required for the extrusion. A similar test procedure is used for determining the gel strength of the absorbent in 1% saline solution. The saline solution is often used for absorbency tests on diapers, sanitary pads and the like because of its physiological similarity to body fluids.

Water Absorption Rate

The water absorption rate (WAR), as used in this specification, is calculated from a measurement of the amount of water absorbed and retained by a sample of the absorbent which is soaked in water for thirty seconds in comparison to the amount of water absorbed and retained by an equal weight of absorbent soaked in water for five minutes. Considering the amount of water retained in the five minute soak to equal 100%, the water absorption rate (WAR) figure is the amount of water retained by the thirty second soak expressed as a percentage of that retained by the five minute soak. In order for an absorptive product to perform satisfactorily in an absorbent pad, the WAR value should be at least as high as 80, indicating that at least 80% as much fluid is absorbed in thirty seconds as in five minutes. The five minute soaking period has been found to be adequate to insure complete saturation in all reasonably absorptive materials.

Water and Saline Retention Values

The Water Retention Value (WRV) and Saline Retention Value (SRV), as used in this specification, are employed to evaluate the absorbency of samples when saturated with water and with saline solution, respectively. In the determination of the SRV, a 1% sodium chloride solution is used to simulate body fluids such as perspiration, blood, urine, etc.

The procedures employed to evaluate the absorbent materials are the same except that distilled water is employed in the WRV determination and 1% NaCl is employed in the SRV determination. The values are determined by the following procedure:

A suction filter flask is provided equipped with a funnel and Whatman No. 1 filter. To this set up, 20 ml. of distilled water or 1% sodium chloride is added and suction is applied until the liquid has drained through. The funnel with wet filter paper is removed and weighed to determine the wet tare weight. Following this, the funnel with wet paper is replaced, approximately 1.0 g of dry crumb hydrolyzed, aged, washed product produced according to the invention is placed on the wet filter paper, 50 ml. of distilled water or of 1% NaCl is poured over the product granules which are allowed to soak 5 minutes after which excess water is removed by suction applied for one minute. The funnel, filter and wet contents are removed and weighed.

$$\genfrac{}{}{0pt}{}{\text{WRV}}{\text{or SRV}} = \frac{(W_2 - W_1) - S}{S}$$

wherein
 WRV = water retention value, g water/g. product
 SRV = salt retention value, g. 1% NaCl/g. product
 $W_1$ = tare weight of the funnel and wet filter paper
 $W_2$ = weight of the funnel containing the soaked sample
 S = weight of the dry sample The following is a specific example of the preparation of the hydrolyzed, polymer-modified cellulosic fiber material which is the starting material for the absorption-enhancing treatment of the present invention.

EXAMPLE 1

1500 grams of bleached southern softwood kraft pulp were added, together with 20 liters of water and 1.8 grams of ferrous ammonium sulfate hexahydrate to a steam jacketed ribbon blendor reactor equipped with a reflux condenser. The pH was adjusted to 3.9 with 10% sulfuric acid. The reactor contents were blanketed with a nitrogen atmosphere and heated to 90° C. to purge the system. The pulp slurry was then cooled to 60° C. and 3.75 liters of inhibitor-free acrylonitrile and 38 milliliters of 10% hydrogen peroxide were added under agitation. After one hour at moderate reflux, the unreacted acrylonitrile monomer was allowed to distill off, leaving a product comprising polyacrylonitrile-modified cellulose fibers in a polymer-to-fiber ratio of about 2 to 1 from which the aqueous reaction medium was removed by filtration to leave the fibrous product in a damp state.

The polyacrylonitrile-modified cellulose was subjected to an alkaline hydrolysis carried out at high solids content as follows:

Three hundred grams of the polymer-grafted cellulose fibers (dry basis) dampened with 200 grams of water were agitated in a ribbon blender while in a crumb-like state and a solution of 150 grams of sodium hydroxide in 350 grams of water were added to the moist graft polymerized cellulose fibers. The resulting mass of 45% solids concentration was heated at 90° C. for 90 minutes under agitation in the ribbon blender. At the end of the hydrolysis period, the reaction product was a crumb-like, damp, porous mass containing cellulose fibers having grafted therein and thereon primarily the sodium salt of polyacrylic acid.

In the above hydrolysis reaction, the solids concentration is at all times so high that the fluid content is insufficient to disperse the solid polymer-grafted fibers, which are merely dampened by the aqueous medium and remain throughout the reaction in a crumb-like state so that the hydrolysis product is a crumbly, porous mass which is easily dried or may be readily washed with water which quickly penetrates the porous structure of the mass and is capable of rapid removal therefrom by filtration.

The above reaction product from the high solids hydrolysis of polymer-grafted cellulose fibers exhibits varying properties in absorbency for aqueous fluids, as measured by water retention value (WRV), saline retention value (SRV) and water absorption rate (WAR), and also varies in gel strength dependent on the factors previously mentioned, as will be hereinafter described.

In the above Example 1, for instance, the hydrolysis was carried out at 45% solids concentration. The resultant product was found to be very receptive to the aging, swelling and conditioning process of this invention, by means of which the absorbency of the material, as measured by water retention value (WRV) and saline retention value (SRV), was improved by 250% over the absorbency of the material as taken from the reaction vessel at the completion of the hydrolysis. The physical consistency of the product, as measured by the gel strength of resistance to deformation or displacement under stress, was completely satisfactory for use in absorptive pads such as disposable diapers, sanitary pads, tampons and incontinence pads.

It has been found, however, that carrying out the hydrolysis at 65% solids concentration yields a product which, although having a very high gel strength, has a substantially lower initial absorptivity and is very much less responsive to the process of this invention, the total degree of improvement in absorptivity achieved by the process when applied to this product being in the range of 50% or less.

Furthermore, if the hydrolysis is carried out at about 30% solids concentration, for example, the product, although responsive in its absorptivity aspect to the conditioning process of this invention, is deficient in gel strength. Because of this factor, as the product becomes saturated with aqueous fluids during use as a diaper, for example, the particulate structure tends to break down under pressure and the absorbent is subject to displacement within the confines of the diaper outer layers.

B. Aging The Hydrolyzed Product

The fluid absorptive and gel strength characteristics of polyacrylate modified cellulose fibers thus derived are altered by storing the hydrolysis product at room temperature for varying periods of time. Increasing the length of the period of storage results in an increase in water absorption rate as well as both the water and salt retention values. These changes, however, are accompanied by corresponding decreases in the gel strength of the polymer-modified material, so that it has not been found possible to obtain, by merely employing simple aging procedures, an absorptive product exhibiting both desirably high absorbency properties and acceptably high structural integrity, as measured by gel strength.

In accordance with the present invention, the crumb hydrolyzed products are allowed to age at room temperature or moderately elevated temperatures for a period of time sufficient to increase the absorptive properties thereof as compared to the fresh hydrolyzed crumb product. In general, the products are aged for a period of at least one, and preferably, three to six weeks before being subjected to the washing and soaking procedure of this invention. The effect of aging may be best explained with reference to Table I wherein a crumb-hydrolyzed product produced as in Example 1 at about 50.5% solids concentration was aged at room temperature for 70 days. Samples removed at various intervals were soaked twice in water, dried and analyzed for polyacrylamide (PAM) and polyacrylic acid (PAA) contents.

TABLE I

| | | | EFFECT OF WET CRUMB AGING | | | | |
|---|---|---|---|---|---|---|---|
| Sample No. | Age, Days | Yield[a] % | WRV g/g | SRV g/g | Nitrogen, % | PAM, % | PAA, PAA, % |
| 1 | 1 | 80 | 17 | 10 | 2.95 | 15.0 | 43 |
| 2 | 7 | 80 | 20 | 10 | 2.70 | 13.7 | 42 |
| 3 | 15 | 80 | 22 | 11 | 2.85 | 14.5 | 41 |
| 4 | 30 | 86 | 23 | 11 | 2.52 | 12.9 | 39 |
| 5 | 50 | 96 | 33 | 13 | 2.25 | 11.4 | 39 |
| 6 | 70 | 82 | 29 | 12 | 2.31 | 11.7 | 36 |

[a]Based on amount of dry product recovered from washing 50 g. of wet hydrolyzed crumb The data of the above Table illustrate that hydrolysis is substantially about 83% complete before any appreciable aging and slowly increases to about 87% after storage for 70 days. The disappearance of carboxyl groups during this period (as indicated by the PAA%) suggests that a cross-linking via esterification with cellulose hydroxyl groups is occurring. It is also believed that during aging, the firm gel developed during hydrolysis gradually weakens resulting in severance of some bridging chains and reformation of macromolecules.

C. Steeping and Swelling of Aged Product

In accordance with the invention, the aged hydrolyzed product is subjected to a steeping and swelling process and is carried out by placing a quantity of the hydrolysis product in at least 20 times its weight of water and, after gentle stirring to ensure complete wetting of each of the particulate masses of fibers, the aqueous slurry is allowed to remain quiescent for a period of time ranging from 10 minutes to as much as an hour or more. The water temperature may vary from cold to moderately warm, ambient temperature being quite suitable. Boiling and strong agitation should be avoided because they tend to fracture and fragment the particulate entities. As the steeping period progresses, the expansion and swelling of the granular masses of fibers may be visually observed, the volume occupied by the solid component of the slurry increasing by from about 15% to as much as 40% within a period of about 15 minutes. As earlier mentioned, the receptiveness of the polymer-modified fibers to the swelling process is variable, dependent on the prior history of the particular sample being treated, and this variable receptiveness is responsible for the variation in the volume change observed.

When the steeping period is completed and no further swelling is evident, the swelled, water saturated gel-like granules or particles may be separated from the fluid medium by filtration or centrifugation and subsequently dried or, if desired, the steeping step may be repeated before drying in order to insure a more complete removal of impurities such as salts, alkali and the like from the gel particles. During the second steeping in an aqueous medium, little or no further swelling of the solid granules will be observed.

D. Drying Hydrolyzed, Aged, Swollen Product

Drying may be carried out at moderately elevated temperatures in a circulating hot air oven, by passing hot air through the damp solids while suspended on a traveling foraminous carrier, or by similar conventional techniques. Moderate care should be exercised to avoid undue fragmentation of the fibrous gel granules before and during drying and excessively high air temperatures should also be avoided because they have been found to deleteriously affect the absorptivity of the granules. For example, a sample of polyacrylate-modified cellulose fibers treated in accordance with the steeping procedure outlined above and dried in an air stream having an air temperature of 250° F. was found to have a WRV of 55, whereas, the same material dried in 325° F. air had a WRV of only 14. In general, temperatures below about 300° F. will be satisfactory herein.

After completion of the steeping and swelling process, the polyacrylate-modified cellulosic fiber material, which is completely saturated with water, is comprised of clumps or agglomerates of fibers in particulate masses which may be described in physical appearance as wet granules of a firm, white swollen, gel-like substance. Drying of the gel under conditions which do not crush or pulverize the individual grains gives an amber, coarsely granular material which is easily rewet by water and which absorbs aqueous fluids very rapidly and in very large amounts.

By the process of the invention, a significant improvement in the absorptive properties of the polymer-modified cellulosic fiber material may be obtained over and above that resulting from merely aging the product and the improvement obtained is accomplished without a significant loss of gel strength. It is therefore possible to stop the aging of the hydrolysis product mass at a point at which the gel strength is still acceptably high and to subject the mass at that time to the soaking procedure in water which greatly enhances the absorptivity of the material. The final product, then, exhibits the hitherto unattainable combined properties of a very high absorptivity and a strong gel structure so that the product is an excellent absorbent but will not lose its structural integrity and become pasty or glutinous when saturated with fluid.

It has been previously mentioned hereinabove that the polymer-modified cellulose products which are of utility in absorptive pads range in polymer-to-fiber ratio from about 0.5 to 1 to as high as 5 to 1, the preferred materials having ratios between 1 to 1 and 3.5 to 1. Within the preferred range, a change in polymer-to-fiber ratio will produce a change in the absorptive properties of the product after hydrolysis. The following Table II illustrates the effect of polymer-to-fiber ratio on absorptive properties when employed at a solids concentration within the preferred range.

TABLE II

EFFECT OF POLYMER-TO-FIBER RATIO ON ABSORPTIVE PROPERTIES
(All Samples Swelled)

| Sample No. | Polymer: Fiber Ratio | Solids % | Sample Age, days | WRV, g./g. | Absorption Rate % | Gel Strength in Water kg./cm$^2$ | SRV g./g. | Gel Strength in 1% NaCl kg./cm. |
|---|---|---|---|---|---|---|---|---|
| A | 1:1 | 50 | 3 | 14 | 96 | 18 | 8 | 19 |
| B | 2:1 | 50 | 8 | 24 | 89 | 11 | 13 | 17 |
| C | 3:1 | 52 | 7 | 35 | 76 | 7 | 14 | 16 |

Table III which follows dramatically illustrates the effect of the critical swelling and aging operations of this invention on the physical properties of the polyacrylate-modified fibers obtained from hydrolysis reactions conducted on natural cellulose fibers modified by graft polymerization of acrylonitrile thereon in a polymer-to-fiber ratio of about 2:1.

The physical properties of the various products were measured on a sample which was dried without undergoing the swelling process and also on a sample which was first swelled in water in accordance with the process of this invention and then dried after storage as indicated.

TABLE III

EFFECT OF SWELLING ON AGED POLYMER-GRAFTED CELLULOSE HYDROLYSIS PRODUCT

| Sample No. | Solids % | Sample age, days | WRV, g./g. No Swell | WRV, g./g. Swell | Absorption Rate, % No Swell | Absorption Rate, % Swell | Gel Strength in Water, kg./cm.$^2$ No Swell | Gel Strength in Water, kg./cm.$^2$ Swell | SRV, g./g. No Swell | SRV, g./g. Swell | Gel Strength in 1% NaCl, kg./cm.$^2$ No Swell | Gel Strength in 1% NaCl, kg./cm.$^2$ Swell |
|---|---|---|---|---|---|---|---|---|---|---|---|---|
| A | 65 | 3 | 11 | 15 | 55 | 96 | 22 | 18 | 5 | 9 | (a) | 120 |
| B | 55 | 50 | 17 | 24 | 45 | 88 | 16 | 10 | 7 | 14 | 32 | 15 |
| C | 50 | 200 | 29 | 45 | 40 | 71 | 6 | 3 | 9 | 18 | 21 | 7 |
| D | 61 | 7 |  | 19 |  | 88 |  | 14 |  | 13 |  | 18 |
|  |  | 13 |  | 23 |  | 92 |  | 11 |  | 14 |  | 15 |
|  |  | 29 |  | 26 |  | 92 |  | 10 |  | 15 |  | 13 |
|  |  | 60 |  | 32 |  | 88 |  | 8 |  | 16 |  | 10 |
| E | 47 | 7 |  | 46 |  | 58 |  | 5 |  | 20 |  | 6 |
|  |  | 13 |  | 55 |  | 43 |  | 4 |  | 21 |  | 5 |
|  |  | 29 |  | 64 |  | 43 |  | 3 |  | 22 |  | 5 |
|  |  | 59 |  | 66 |  | 33 |  | 3 |  | 20 |  | 6 |

(a)Too high to measure.

It will be noted from the above Table III that Products B and C, prepared by hydrolysis at 55 and 50% solids, respectively, show very substantial increases in absorptive qualities when subjected to the swelling process, whereas Product A, prepared by a high (65%) solids content hydrolysis, is substantially less responsive. It is also to be particularly noted that the highly desirable improvement in absorptive properties in Products B and C is achieved by the swelling process of this invention without loss in gel strength below the level needed to function in absorptive pads. The resultant products are therefore uniquely qualified to serve as absorbents in pads of various types since they exhibit a hitherto unattainable combination of very high absorptiveness for aqueous fluids together with a structural integrity which overcomes the tendencies toward oozing displacement of the saturated absorbent material which was characteristic of previously available high WRV materials.

It will also be seen from Table III that the effectiveness of the swelling procedure in improving the water retention value (WRV) of polyacrylate-grafted cellulose fibers varies substantially depending on the prior history of the fibers when subjected to the swelling procedure. If the hydrolysis step has been carried out at a solids concentration approaching 65%, the initial WRV of the product will be relatively low, the gel strength relatively high and the swelling procedure will serve to increase the WRV only moderately. If, however, the hydrolysis step has been carried out within the preferred range of 35-55% solids concentration, the gel strength and WRV will both be within the desired range of values and the WRV will increase very substantially upon being subjected to the swelling step considered essential to this invention. The increase in WRV which occurs during the swelling is obtained without substantial loss in gel strength, thus producing a material having a very substantially improved WRV while retaining a gel strength within the range which is considered satisfactory for use in a variety of absorptive pads.

Heretofore, an increase in WRV had been associated with a decrease in gel strength and polymer-grafted materials having very desirably high WRV's were completely unsatisfactory for use as absorbents in diapers, for example, because the agglomerates disintegrated completely upon saturation with an aqueous fluid to become undesirably slippery and gelatinous. The resulting mucilaginous paste was displaceable within the diaper under even slight pressure and tended to ooze through the pores of the permeable inner liner sheet of the diaper.

The improvement in WRV which results when polyacrylate-grafted cellulose fibers having the proper prior history are subjected to the aging and swelling process of this invention is essential to the production of an absorptive material having the most desirable combination of physical properties for use in disposable diapers, tampons, sanitary pads, incontinence pads, surgical and general hospital pads.

I claim:

1. In a process for modifying cellulosic material to produce absorbent and structural integrity characteristics therein, said process comprising treating an aqueous slurry of said cellulosic material fibers with an ethylenically unsaturated compound containing at least one functional moiety selected from the group consisting of acrylamido, acyl halide, nitrile, ester, alkenyl halide, carboxylate and carboxyl to effect polymerization onto said cellulosic material, the improvement which comprises:
   a. hydrolyzing or neutralizing said modified cellulosic material fibers at a total solids concentration of between about 35 to about 60% to form a graft copolymer of cellulosic fibers and an alkali metal salt of said ethylenically unsaturated compound, said hydrolyzed product being a porous, crumb-like agglomerated, particulate mass;
   b. aging said hydrolyzed crumb product for a period of time sufficient to increase the absorptive properties thereof as compared to the absorptive properties of the fresh hydrolyzed crumb product;
   c. soaking said aged crumb product in water for a period of time sufficient to saturate said mass with water and swell the particles of said material; and
   d. drying said particulate swollen product to remove excess water therefrom under conditions which avoid fragmentation or pulverization of the dried agglomerated product.

2. The process of claim 1 wherein said ethylenically unsaturated compound is acrylonitrile.

3. The process of claim 1 wherein said hydrolyzed product is aged for a period of at least one week.

4. The process of claim 1 wherein said hydrolyzed aged product is soaked in water at room temperature for a period of time ranging from about 10 to about 60 minutes.

5. The process of claim 4 wherein said hydrolyzed aged product is first agitated in water then remains quiescent for said period of time.

6. The process of claim 1 wherein said swollen product is filtered to remove excess water and dried on a foraminous carrier by circulation of hot air.

7. The process of claim 6 wherein said swollen product is dried at a temperature below about 300° F.

8. The process of claim 4 wherein said hydrolyzed aged product is subjected to two soaking steps as defined therein.

9. In a process for modifying cellulosic material to produce absorbent and structural integrity characteristics therein, said process comprising treating an aqueous slurry of natural cellulosic fibers with acrylonitrile to effect polymerization onto said fibers, the improvement which comprises:
 a. hydrolyzing said acrylonitrile modified-cellulosic fibers at a total solids concentration of from about 35 to about 55% to convert a major proportion of said acrylonitrile groups to alkali metal salts of acrylic acid, said hydrolyzed product being a porous, crumb-like agglomerated particulate mass;
 b. aging said hydrolyzed crumb product for a period of time sufficient to increase the absorptive properties thereof over the hydrolyzed, unaged crumb product;
 c. soaking said aged crumb product in water for a period of time sufficient to saturate said mass with water
 d. drying said particulate swollen product to remove excess water therefrom under conditions which avoid fragmentation or pulverization of the dried agglomerated product.

10. A dry cellulosic material graft polymerized with a polymer of an ethylenically unsaturated compound containing at least one functional moiety selected from the group consisting of acrylamido, acyl halide, nitrile, ester, alkenyl halide, carboxylate and carboxyl;
 said product having been obtained by a process comprising hydrolyzing or neutralizing the polymerized product at a solids concentration of from about 35% to about 55%, aging of the resultant hydrolyzed or neutralized product in water to saturate and swell the particulate material and drying under conditions which avoid fragmentation or pulverization of the dried product;
 said dry cellulosic material exhibiting the combined capacities of rapid absorption of fluids, retention of said absorbed fluids when subjected to pressure forces and retention of structural integrity under stress when substantially saturated with fluid.

11. A dry cellulosic material as claimed in claim 10 wherein said material is derived from the in situ graft polymerization of acrylonitrile on natural cellulose fibers.

12. A dry cellulosic material as claimed in claim 10 wherein said material exhibits a capacity to retain its structural integrity when substantially saturated with fluid when subjected to a force of at least 2 kilograms per square centimeter.

13. A dry cellulosic material as claimed in claim 12 wherein said material is derived from the graft polymerization of acrylonitrile on natural cellulose fibers; said acrylonitrile-modified product is hydrolyzed at a solids concentration of from about 45% to about 55%; said hydrolyzed product is aged for a period of about three to six weeks; said aged product is soaked and swelled in water for from about 10 to 60 minutes and said swelled product is dried at a temperature below about 300° F.

* * * * *